(12) United States Patent
Xiao et al.

(10) Patent No.: US 11,497,636 B2
(45) Date of Patent: Nov. 15, 2022

(54) VASCULAR STENT (71) Applicant: Lifetech Scientific (Shenzhen) Co., Ltd., Shenzhen (CN)

(72) Inventors: Benhao Xiao, Shenzhen (CN); Yifei Wang, Shenzhen (CN)

(73) Assignee: Lifetech Scientific (Shenzhen) Co. Ltd., Shenzhen (CN)

(*) Notice: Subject to any disclaimer, the term of this patent is extended or adjusted under 35 U.S.C. 154(b) by 725 days.

(21) Appl. No.: 16/346,195

(22) PCT Filed: May 10, 2017

(86) PCT No.: PCT/CN2017/083721
§ 371 (c)(1),
(2) Date: Apr. 30, 2019

(87) PCT Pub. No.: WO2018/082278
PCT Pub. Date: May 11, 2018

(65) Prior Publication Data
US 2019/0290460 A1  Sep. 26, 2019

(30) Foreign Application Priority Data
Nov. 4, 2016 (CN) .......................... 201610962664.5

(51) Int. Cl.
*A61F 2/90* (2013.01)
*A61F 2/07* (2013.01)
(Continued)

(52) U.S. Cl.
CPC .................. *A61F 2/89* (2013.01); *A61F 2/07* (2013.01); *A61F 2/852* (2013.01); *A61F 2/856* (2013.01); *A61F 2/90* (2013.01)

(58) Field of Classification Search
CPC .. A61F 2/90; A61F 2/915; A61F 2/954; A61F 2002/828; A61F 2002/91558; A61F 2002/91575
See application file for complete search history.

(56) References Cited

U.S. PATENT DOCUMENTS 6,187,036 B1 * 2/2001 Shaolian .................. A61F 2/90
623/1.1
2016/0008149 A1 1/2016 Hsiao et al.

FOREIGN PATENT DOCUMENTS

| CN | 103961193 A | 8/2014 |
|---|---|---|
| CN | 105662666 A | 5/2016 |

(Continued)

OTHER PUBLICATIONS

First Office Action for corresponding China Application No. 201610962664.5.
Response to First Office Action for corresponding China Application No. 201610962664.5.
Second Office Action for corresponding China Application No. 201610962664.5.
(Continued)

*Primary Examiner* — Diane D Yabut
*Assistant Examiner* — Christian D. Knauss
(74) *Attorney, Agent, or Firm* — Raymond Sun (57) ABSTRACT

A vascular stent (100) comprises a plurality of wave loops. In its natural state, in two of the wave loops which are adjacent in a group, a part of a wave crest of a lower layer wave loop are in a restrained connection with a part of a wave trough of an upper layer wave loop; the other part of the wave crest of the lower layer wave loop passes through the other part of the wave trough of the upper layer wave loop, and the other part of the wave crest and the other part of the wave trough are in a non-contact mutually-suspended connection. Some of the wave crests and wave troughs of the vascular stent (100) are in the non-contact mutually-suspended connection rather than the restrained connection, so that the maximum flexibility is provided to the stent, and meanwhile, the overall stability of the stent is guaranteed.

(Continued)

The stent (100) can maintain a good shape during both implantation and the release process, so that safety during release is ensured.

14 Claims, 11 Drawing Sheets (51) Int. Cl.
*A61F 2/852* (2013.01)
*A61F 2/89* (2013.01)
*A61F 2/856* (2013.01)

(56) References Cited

FOREIGN PATENT DOCUMENTS

| | | |
|---|---|---|
| CN | 105662666 A | 6/2016 |
| CN | 205459226 U | 8/2016 |
| WO | WO03037397 A2 | 5/2005 |
| WO | WO2011034795 A1 | 3/2011 |

OTHER PUBLICATIONS

Response to Second Office Action for corresponding China Application No. 201610962664.5.
Notice of Grant for corresponding China Application No. 201610962664.5.
Granted Patent No. CN 108013955 B for corresponding China Application No. 201610962664.5.
International Search Report dated Jun. 7, 2017 for corresponding PCT Application No. PCT/CN2017/083721.

\* cited by examiner

Exploded view

Exploded view

Fig.6-2

Exploded view

Fig.6-3

Exploded view

Exploded view

VASCULAR STENT

FIELD

The present application relates to the technical field of interventional medical devices, and more particularly relates to a vascular stent.

BACKGROUND

Figure 1:
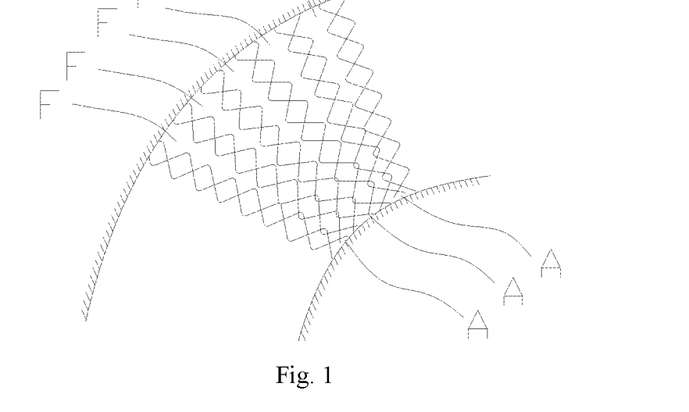
FIG. 1 is a schematic diagram of the flexibility of a conventional nickel-titanium woven-wire stent being implanted into a vessel.
Figure 21:
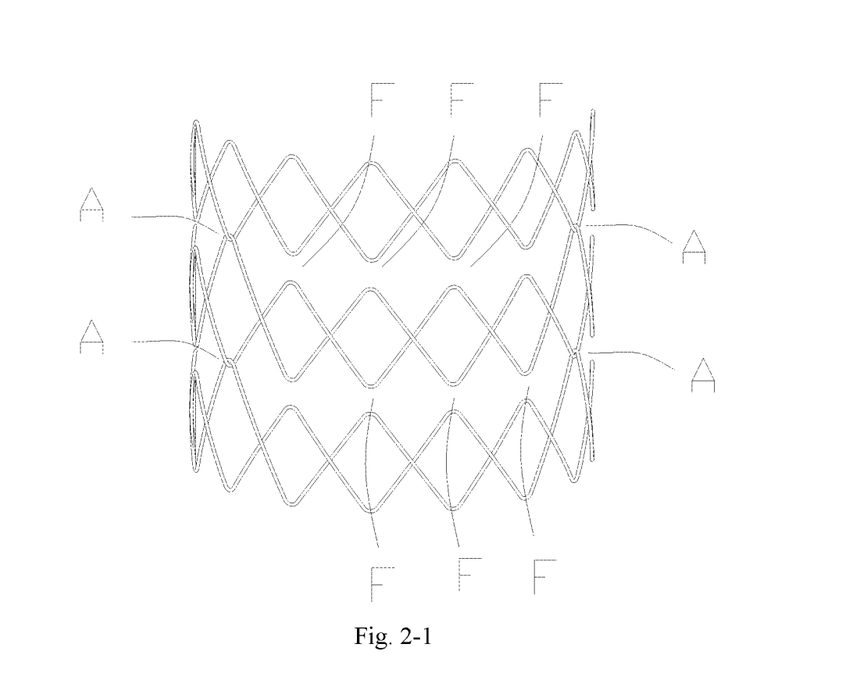
Figure 22:
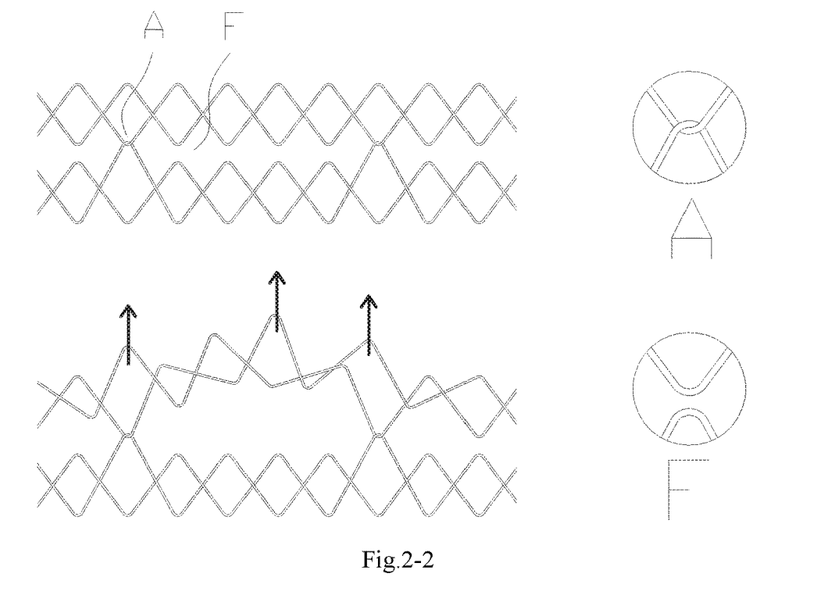

Self-expanding type vascular bare stents are generally divided into nickel-titanium tube-cut stents and nickel-titanium woven-wire stents. The nickel-titanium woven-wire stent is required to have relatively high flexibility in compliance with the vascular anatomic shape. Accordingly, referring to FIG. 1, it is required that at least part of the positions of the wave loops can move within a range after the woven stent is implanted into the vessel. To meet the requirement for shape change, the bare stent may have the structure as shown in FIG. 2-1, where at least two mutually separated wave crests in one wave loop and at least two mutually separated wave troughs in another wave loop adjacent to the wave loop are fixedly connected to form a connection point A, and other wave crests and wave troughs in the two wave loops are suspended and not connected. The bare stent may be adhered effectively to the vascular wall after implantation, but the disconnected wave crests and wave troughs in two adjacent wave loops can easily deform in an excessive manner as shown in FIG. 2-2, which results in the stent having low structural stability. In addition, during the process of assembling the stent, the shape of the stent might not be effectively controlled because of the small number of mutual restriction points between the wave loops, so that assembly of the stent can be rendered more difficult. During the process of releasing the stent, the disconnected wave crests and wave troughs in the wave loops are loose, so that the stent might not be able to retain its shape when the stent exits a sheath, which in some severe cases may even result in injury to the vascular wall.

The stability and the flexibility of the stent may be adjusted by adjusting the proportions and the arrangement mode of the connection points A and suspensions F. If there are more connection points A, the stent is more stable, and the flexibility is reduced. On the contrary, if the flexibility of the stent is improved, the stability is reduced. However, it is not possible for the stent to have stability, a shape that minimizes injury, a safe and reliable releasing performance, and to also conform to the complicated shape of the vasculature.

SUMMARY

The present application provides a vascular stent, including multiple wave loops arrayed along an axial direction. In a natural state, in one group of two adjacent wave loops, part of the wave crests of the lower layer wave loop and part of the wave troughs of the upper layer wave loop are in a restrained connection, and another part of the wave crests of the lower layer wave loop passes through the wave troughs of the upper layer wave loop, and the wave crests and the wave troughs are in a non-contact and mutually-suspended connection. In the natural state, the non-contact and mutually-suspended connection is characterized by the wave crests of the lower layer wave loop and the wave troughs of the upper layer wave loop being intertwined, and the vertices of the wave crests are kept a certain distance from those of the wave troughs. If and only if the stent is axially tensioned, the wave troughs and the wave crests would be in mutual contact and restriction so as to restrict the stent from extending.

Each wave loop is composed of multiple circumferentially arranged waveforms including wave crests, wave troughs and rod bodies connecting adjacent wave crests and wave troughs. The wave troughs of the same wave loop are circumferentially aligned, and the wave crests vary in height. Different positional relationships between the wave crests of varied height and corresponding wave troughs of the upper layer wave loop can be achieved, including a restrained connection A of wave crests/wave troughs and a non-contact and mutually-suspended connection B (mutually suspended and in no contact in the natural state) of wave crests/wave troughs.

In one embodiment, the wave crests which are in the non-contact and mutually-suspended connection with the wave troughs are located on the lesser curvature side region of the vascular stent, and have a vertex angle everted by an angle α. For waveforms adopting the non-contact and mutually-suspended connection points B, the wave crests of the lower layer wave loop are relatively high, and when the stent bends towards the lesser curvature side, mutual displacements/torsions of the waveforms cause warping of the relatively high wave crests. Thus, a certain risk of scratching exists when the delivery system is withdrawn, as movement of the waveforms may be caused by scratching of the delivery system and the wave loops, and the warping wave crests would have an impact on the haemodynamics. After the stent is released at the predetermined position, the vertex angle that is everted by the angle α may effectively diminish the protrusion of the wave crests, so that the adherence effect of the lesser curvature side of the stent is improved, and the risk of displacement/deformation/turning caused by scratching from the delivery system to the bare stent is lowered.

However, when arranged on the greater curvature side of the stent, the protruding vertex angle everted by the angle α may not be adhered to the vessel wall, which would reduce the adherence performance of the greater curvature side of the stent. In addition, when the stent is large relative to the vessel, the protruding everted vertex angle parts would cause stimulation to the vessel wall and even injure the vessel wall, so that the distribution number and the positions of the everted vertex angles have to be designed based on specific clinical requirements. When the stent is required to be adapted for use with a complicated and changing vasculature environment, more everted vertex angle parts may be used to optimize the lesser curvature side of the stent.

In one embodiment, in another group of two adjacent wave loops, part of the wave crests of the lower layer wave loop and part of the wave troughs of the upper layer wave loop are in the restrained connection, and another part of the wave crests of the lower layer wave loop and the part of the wave troughs of the upper layer wave loop are suspended. The waveforms on the side that is opposite to a branch vessel of the stent are suspended, so a simple solution may be provided for fenestration and placement of a branch stent during operation.

In one embodiment, in one group of two adjacent wave loops, the wave crests of the lower layer wave loop and the wave troughs of the upper layer wave loop further include suspended wave crests and wave troughs in addition to those in the restrained connection and in the non-contact and mutually-suspended connection. For example, the vascular stent may be used in an aortic arch operation, or used together with a branch stent after circumferential in-situ fenestration.

In one embodiment, the distances between the vertices of at least two groups of wave crests and wave troughs in the non-contact and mutually-suspended connection are not equal, so that the stent can adapt to an angled aorta, and improve the adherence as well. When the stent adapts to an angled aorta, there would not be too many warping wave crests/wave troughs on the inner wall of the stent. Thus, the lesser curvature side is smooth, and the greater curvature side opens fully and may be completely adhered to the wall.

In one embodiment, in the natural state, the distances between the vertices of the wave crests of the lower layer wave loop and the vertices of the wave troughs of the upper layer wave loop, where the wave crests of the lower layer wave loop and the wave troughs of the upper layer wave loop are in the non-contact and mutually-suspended connection, are ¼ to ⅓ of a waveform height of the wave troughs of the upper layer wave loop. The waveforms of the upper and lower layer wave loops connected by adopting this connection mode may move axially closer to and further from each other, which would greatly improve the flexibility of the stent. In addition, when the region has an obvious expansion deformation, the wave troughs of the upper layer wave loop and the wave crests of the lower layer wave loop are in contact to form a restriction so as to restrict the waveforms and prevent the shape of the stent from being further deformed. Two wave loops are taken for example. When the stent is subjected to axial tensile stress, the waveforms of the upper layer wave loop and the lower layer wave loop which adopt the restrained connection points A will not move, and the waveforms of the upper layer wave loop and the lower layer wave loop which have the connection points B will move closer to each other, and are finally in contact with each other to restrict further extension of the stent. Finally, the axial length H of the stent is increased to H2, and without considering the deformation of the waveforms, the elongation (H2−H) of the stent is generally less than or equal to the distances L2 between the vertices of the wave crests of the lower layer wave loop and the vertices of the wave troughs of the upper layer wave loop, where the wave crests of the lower layer wave loop and the wave troughs of the upper layer wave loop form non-contact and mutually-suspended connection points B.

In one embodiment, the angle $\alpha$ is between 20 and 30 degrees.

In one embodiment, the heights of the vertex angle everted along the axial direction of the vascular stent are less than or equal to the distances between the vertices of the wave crests of the lower layer wave loop and the vertices of the wave troughs of the upper layer wave loop, which are in the non-contact and mutually-suspended connection.

In one embodiment, the wave troughs of the lower layer wave loop are located on a circular ring coaxial with the axis of the vascular stent, and the lower layer wave loop which is in the non-contact and mutually-suspended connection with the upper layer wave loop has different wave heights.

In one embodiment, there are 2 to 4 suspended wave crests and 2 to 4 suspended wave troughs. The numbers of the suspended wave crests and wave troughs are correspondingly adjusted according to a specific part where the stent is used and the diameter of the branch vessel. If the diameter of the branch vessel is larger, more suspended wave crests and wave troughs will be provided.

When the stent is released, the restrained connection guarantees the basic shape and a relatively low elongation of the stent, and the wave crests and the wave troughs which are in the non-contact and mutually-suspended connection and suspended provide relatively high flexibility for the stent. After the stent is located and released, the waveforms may be separated farther from the original distances of the suspended wave crests and wave troughs so as to provide a space for implantation of a branch stent. A branch stent delivery may be easily passed through regions where the suspended wave crests and wave troughs are located. Meanwhile, because of the relatively large degrees of freedom in the suspended regions, and the mutually unrestricted waveforms, the released branch stent in the suspended region would not suffer from relatively high rebound squeeze pressure from the aorta stent, so that smooth blood flow along the branch vessel may be guaranteed.

In one embodiment, the vascular stent further includes a stent graft section. The multiple wave loops form a bare stent which is connected with one end of the stent graft section. For example, the vascular vessel may be an abdominal aorta stent graft. In one embodiment, the vascular vessel includes an inner-layer stent and an outer-layer stent. The outer-layer stent is arranged outside and surrounds the inner-layer stent, and at least one end of the outer-layer stent is hermetically connected with the outer surface of the inner-layer stent. The inner-layer stent includes a metal stent and a coating membrane covering the surface of the metal stent. For example, the outer-layer stent may be of a skirt shape, with one end hermetically connected to the surface of the inner-layer stent and the other end provided with an opening. For another example, the outer-layer stent is of a lantern shape, with both ends hermetically connected to the surface of the inner-layer stent.

In one embodiment, the connection points of the restrained connection are uniformly distributed in the circumferential direction of the vascular stent, and their connecting line in the axial direction is a spiral line. Provided with the axial tensile strength by the restrained connection points, the multilayer wave loop stent formed by adopting the arrangement mode is stable in structure, experiences minimal axial elongation, and has a partially shortened space. The wave loops positioned close to each other provides the flexibility to a certain extent. The connection points A, the connecting line of which in the axial direction is the spiral line, eliminate the directivity of the overall physical property of the stent. The non-contact and mutually-suspended connection points B may allow the wave crests/wave troughs adopting this connection mode to be in relatively free and mutually non-interfering states. The wave loops in this state have a certain displacement/deformation space in the axial direction and may relatively move closer or further away to improve the flexibility of the stent.

In one embodiment, part of the wave crests of the lower layer wave loop and part of the wave troughs of the upper layer wave loop are fixedly connected to form the restrained connection, or part of the wave crests of the lower layer wave loop pass through part of the wave troughs of the upper layer wave loop and are in direct contact with the wave troughs to form the restrained connection. By adoption of the above-mentioned mode, the upper and lower layers of wave loops of the stent may be connected, and the wave loops may also be positioned close to one another in the axial direction. When the stent bends and the connection points are located on the lesser curvature side, the wave loops are positioned close to one another to improve the overall flexibility of the stent.

In one embodiment, each wave loop has 8 waveforms.

According to the present application, one or more non-contact and mutually-suspended connections are adopted on the woven stent to replace part of the restrained connections. The wave troughs of the upper layer wave loop and the wave crests of the lower layer wave loop are intertwined in the natural state, and their vertices may be in contact with each other only when the stent stretches, so that the stent is provided not only with maximum flexibility, but also guaranteed overall stability. The stent can maintain a good shape during both assembly and release, thus guaranteeing safety during release.

BRIEF DESCRIPTION OF THE DRAWINGS

The present application will be further described below in combination with accompanying drawings and embodiments. In the drawings:

FIG. 2-1 is a structural schematic diagram of a conventional bare stent having mutually restricted wave crests/wave troughs and suspended wave crests/wave troughs;

FIG. 2-2 is a schematic diagram of the deformation of the bare stent of FIG. 2-1 under stress;

FIG. 3-1 is a structural schematic diagram of a stent according to Embodiment 1 of the present invention;

FIG. 3-2 is a structural schematic diagram of the stent of Embodiment 1 shown with the stent axially cut and spread out;

FIG. 3-3 is a schematic diagram of the structure of the stent of Embodiment 1 shown spread out when under tensile stress;

FIG. 4-1 is a schematic diagram illustrating the uniform release the stent of Embodiment 1 from a sheath in a step by step manner;

FIG. 4-2 is a schematic diagram illustrating the sudden expansion of wave loops during the release of a conventional stent;

FIG. 5-1 is a schematic diagram illustrating warping wave crests of the lesser curvature side when the stent provided with connection points B is positioned on the lesser curvature side bends;

FIG. 5-2 is a structural schematic diagram of a stent according to Embodiment 2 of the present invention;

FIG. 5-3 is a schematic diagram of a height and an everted angle α of the stent of Embodiment 2;

FIG. 5-4 is a cross sectional view of the stent of Embodiment 2;

FIG. 5-5 is a schematic diagram illustrating non-warping wave crests of the lesser curvature side when the stent of Embodiment 2 bends;

FIG. 6-1 is a structural schematic diagram of a stent according to Embodiment 3 of the present invention;

FIG. 6-2 is a structural schematic diagram of the stent of Embodiment 3 shown with the stent axially cut and spread out;

FIG. 6-3 is a schematic diagram of the structure of the stent of Embodiment 3 shown spread out, in which a branch stent is implanted;

FIG. 7-1 is a structural schematic diagram of a stent according to Embodiment 4 of the present invention;

FIG. 7-2 is an enlarged schematic diagram of a connection point BC of the stent of Embodiment 4;

FIG. 7-3 is a schematic diagram showing an adherence effect of the stent of Embodiment 4;

FIG. 7-4 is a schematic diagram of a height of an everted angle α of the stent of Embodiment 4;

FIG. 8-1 is a structural schematic diagram of a membrane-coated stent according to Embodiment 5 of the present invention;

FIG. 8-2 is a schematic diagram illustrating a swinging effect of the membrane-coated stent of Embodiment 5;

FIG. 8-3 is a schematic diagram illustrating the beak phenomenon of a conventional stent in an anchoring region;

FIG. 9-1 is a structural schematic diagram of a chimney stent according to Embodiment 6 of the present invention;

FIG. 9-2 is a partial enlarged schematic diagram of the chimney stent of Embodiment 6;

FIG. 10-1 is a structural schematic diagram of a chimney stent according to Embodiment 7 of the present invention; and FIG. 10-2 is a partial enlarged schematic diagram of the chimney stent of Embodiment 7.

DETAILED DESCRIPTION

To more clearly understand the technical features, objectives and effects of the present application, specific implementation modes of the present application are described in detail now in combination with the accompanying drawings.

Unless otherwise defined, all technical and scientific terms used herein are the same as meanings of general understandings of persons skilled in the art of the present application. In this disclosure, the terms used in the description of the present application are only used to describe specific embodiments, but not intended to limit the present application.

According to a vascular stent provided by the present application, in a natural state, in one group of two adjacent wave loops, one part of the wave crests of a lower layer wave loop and one part of the wave troughs of an upper layer wave loop are in a restrained connection, and another part of the wave crests of the lower layer wave loop passes through the wave troughs of the upper layer wave loop, and the wave crests and wave troughs are in a non-contacting and mutually-suspended connection.

According to the different applicable environments, the wave height and the arrangement of two connection modes may be specifically adjusted during the design:

(1) in the non-contact and mutually-suspended connection mode, the distances between the vertices of the wave crests of the lower layer wave loop and the vertices of the wave troughs of the upper layer wave loop determine the range of the distance between which two adjacent wave loops are separated from each other. In other words, the distances between the vertices of the wave crests and the vertices of the wave troughs of the connection points are increased by adjusting the heights of the wave crests, so that the degree of freedom between the wave loops of the stent may be effectively increased, so that the flexibility is improved.

(2) The arrangement mode of the two connection modes described herein is not the only possible arrangement mode. The axial elongation of the stent is provided by the restrained connection points A, and the connection points A would determine the length and the appearance of the stent in its natural state. When the stent has a bending deformation, the wave loops would experience relative movement and twisting. Corresponding wave crests/wave troughs of the upper layer wave loop and the lower layer wave loop which are located on the greater curvature side would be spaced relatively further from each other, and corresponding wave crests/wave troughs of the upper layer wave loop and the lower layer wave loop which are located on the lesser curvature side would be spaced relatively closer to each other, thereby allowing the stent to have the requisite flexibility. In this state, because the wave crests/wave troughs cannot separate from each other at great distances, the wave crests/wave troughs which are connected through the restrained connection points A would directly restrict the bending flexibility of the stent when located on the greater curvature side. The non-contact and mutually-suspended connection points B can provide a certain space for the wave crests/wave troughs to separate from each other for greater distances, and therefore defines the stretching range of the stent. When the wave crests/wave troughs on the greater curvature side of the stent are comprised entirely of the non-contact and mutually-suspended connection points B, the flexibility is higher, but too many connection points B could easily result in the increase of the elongation of this region. Therefore, when the stability and the elongation are taken into special consideration during the design of the stent, the proportion of the number of the connection points A that are distributed circumferentially may be properly increased, and the connection points B are arranged at key positions that are in need of flexibility to improve the flexibility. When the stent is designed to be applied to a lesion position of a complicated vascular or zigzag anatomic shape, the stent is required to have higher flexibility. For this situation, the distribution proportion of the connection points B may be increased, and the connection points A are only arranged at key points that need to be stressed, so as to control the shape of the stent.

During assembly, as the wave loops of the vascular stent of the present application are mutually connected, the waveforms are restricted, and the relative movement of the wave loops is limited. When the vascular stent is gradually collected into the sheath, restriction between the wave loops allows the shape change of the waveforms in the sheath to be uniformly transmitted to the waveforms to be surrounded outside the sheath. Compared with a conventional vascular stent in the prior art, the vascular stent of the present invention can be more easily inserted into the sheath in an orderly manner, so that the outward turns of the waveforms caused by squeezing and dragging during assembly, and even damage to the shape of the stent, can be avoided. Similarly, when the delivery system reaches the appointed position and the stent is slowly released from the sheath, the vascular stent of the present application can maintain a good shape and be uniformly gradually released from the sheath without causing the sudden expansion of the wave loops, so that injury to the vascular wall can be avoided.

Embodiment 1

Figure 31:
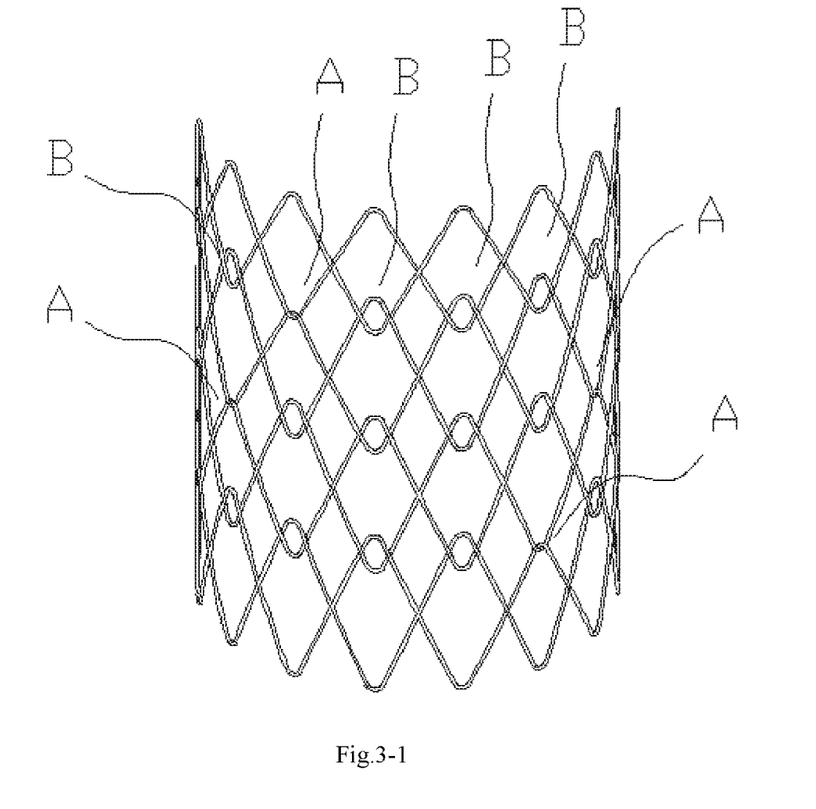

Referring to FIG. 3-1, the vascular stent of the present embodiment is a bare stent 100, which is a woven mesh tubular structure and includes multiple wave loops woven from nickel-titanium wires and distributed along an axial direction. Each wave loop includes multiple circumferentially arrayed waveforms. Each waveform includes multiple wave crests and wave troughs which are distributed in an alternating manner. In two adjacent wave loops, the wave crests of a lower layer wave loop are opposite to the wave troughs of an upper layer wave loop. All the wave troughs of the same wave loop are circumferentially aligned, namely the vertices of all the wave troughs of the same wave loop are located on a circular ring coaxial with the axis of the bare stent. The wave crests of the same wave loop have different heights. By providing the wave crests with different heights, it is possible to obtain different positional relationships between the corresponding wave crests and wave troughs in the lower layer wave loop and the upper layer wave loop. The positional relationships may be wave crests/wave troughs (corresponding to the connection points A as shown in FIG. 3-1) that are in a restrained connection, and wave crests/wave troughs (corresponding to the connection points B as shown in FIG. 3-1) that are in a non-contact and mutually-suspended connection. The connection points A are the vertices of the wave troughs of the upper layer wave loop in a natural state that are in contact with the vertices of the wave crests of the lower layer wave loop. The connection points B are the wave troughs of the upper layer wave loop in the natural state that pass through the wave crests of the lower layer wave loop, and the vertices of the wave troughs of the upper layer wave loop and the vertices of the wave crests of the lower layer wave loop are separated by a distance. The wave crests/wave troughs in restrained connection corresponding to the connection points A may be connected by various modes. For example, the wave crests of the lower layer wave loop pass through the wave troughs of the upper layer wave loop, and the vertices of the wave crests and the wave troughs are in direct contact and in a movable connection with each other; namely when the bare stent is compressed along the axial direction, the wave troughs of the upper layer wave loop and the wave crests of the lower layer wave loop may move relative to each other until they are separated by a distance, but after the axial compression force is withdrawn, the wave troughs of the upper layer wave loop and the wave crests of the lower layer wave loop are restored until their vertices are in mutual contact. The wave troughs that correspond to the connection points A of the upper layer wave loop may also be directly and fixedly connected with the wave crests of the lower layer wave loop; namely when the bare stent is compressed along the axial direction, the wave troughs of the upper layer wave loop and the wave crests of the lower layer wave loop would not move relative to each other. In other embodiments of the present application, the wave troughs that correspond to the connection points A of the upper layer wave loop may also be fixedly connected with the wave crests of the lower layer wave loop through connecting pieces.

Figure 32:
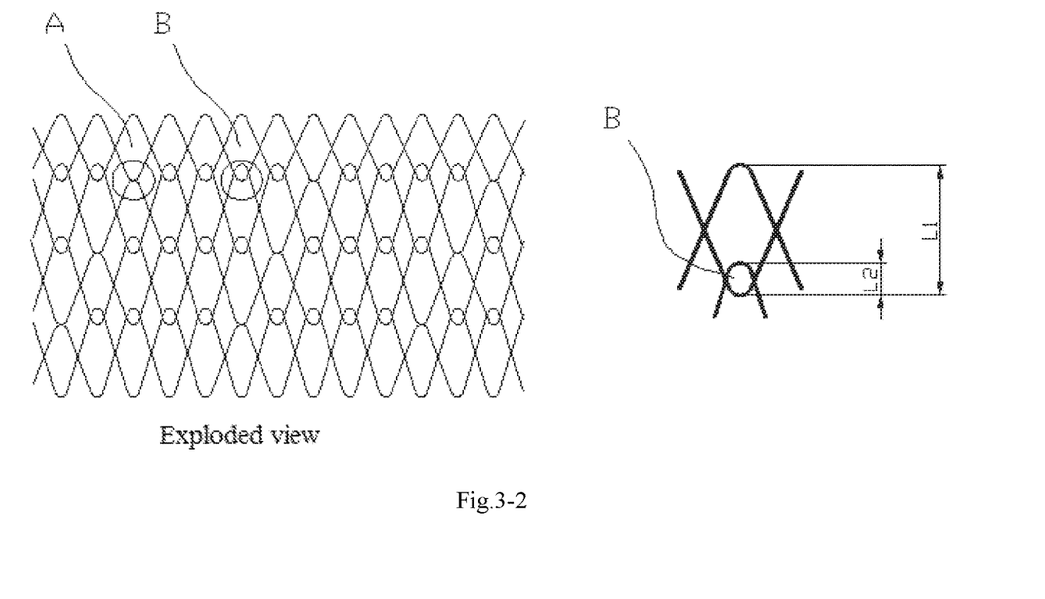
Figure 33:
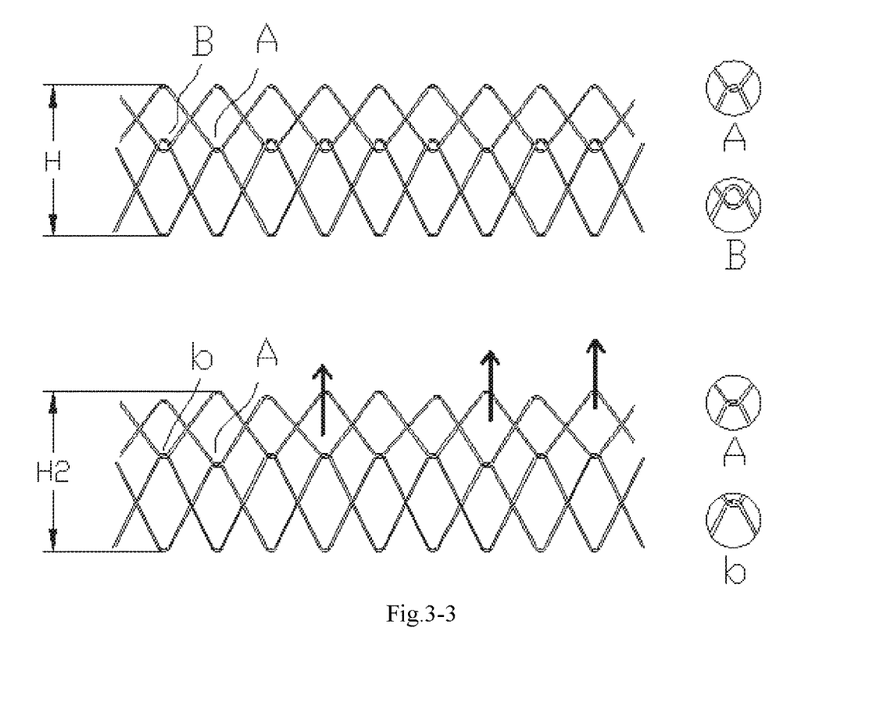

In the bare stein of the present embodiment, referring to FIG. 3-2, the wave troughs that correspond to the connection points A of the upper layer wave loop and the wave crests of the lower layer wave loop are movably connected, so that the connection between the upper layer wave loop and the lower layer wave loop of the stent may be achieved; and it is also possible to move the wave loops close to one another in the axial direction. When the stent bends and the connection points A are located on the lesser curvature side, the wave loops can move closer towards each other to improve the overall flexibility of the stent. The connection points B correspond to the wave crests/wave troughs in a non-contact and mutually-suspended connection. During weaving, the wave crests of the lower layer wave loop pass through the wave troughs of the upper layer wave loop, and the wave troughs of the upper layer wave loop and the wave crests of the lower layer wave loop are separated by a distance. At the connection points B, it is desirable that the distances L2 between the vertices of the wave crests of the lower layer wave loop and the vertices of the wave troughs of the upper layer wave loop, where the wave crests of the lower layer wave loop and the wave troughs of the upper layer wave loop are in a non-contact and mutually-suspended connection, are ¼ to ⅓ of the waveform height of the upper layer wave loop. The waveforms of the upper and lower layer wave loops connected with this type of non-contact mutually-suspended connection may move axially closer to and further from each other within the range of the distances L2 between the vertices of the wave crests of the lower layer wave loop and the vertices of the wave troughs of the upper layer wave loop, so that the flexibility of the stent is greatly improved. When the stent region corresponding to the connection points B has an obvious expansion deformation, the wave troughs of the upper layer wave loop and the wave crests of the lower layer wave loop may move to be in mutual contact to form a restriction so as to prevent the shape of the stent from being further deformed. As shown in FIG. 3-3, two wave loops are taken for example. When the stent is subjected to axial tensile stress, the waveforms of the upper layer wave loop and the lower layer wave loop which have the connection points A will not move, and the waveforms of the upper layer wave loop and the lower layer wave loop which have the connection points B will move closer to each other, and are finally in contact with each other to restrict further extension of the stent. Finally, the axial length H of the stent is stretched to H2, and without considering the deformation of the waveforms, the elongation (H2−H) of the stent is generally less than or equal to the distances L2 between the vertices of the wave crests of the lower layer wave loop and the vertices of the wave troughs of the upper layer wave loop of the connection points B.

Figure 41:
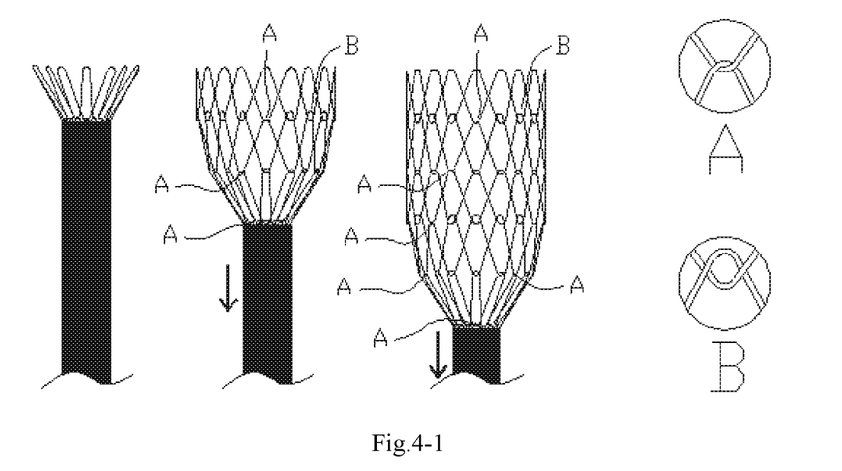
Figure 42:
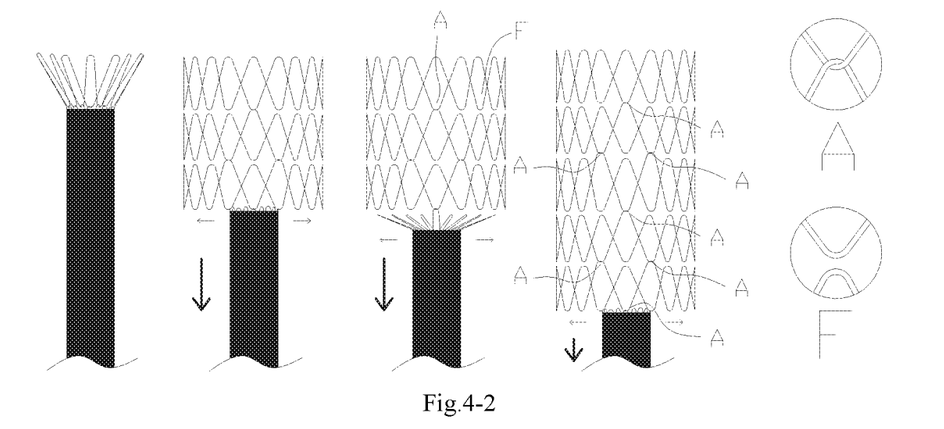

During the assembly process, the range of the relative movement between the wave loops of the woven bare stent is limited. When the bare stent is collected into the sheath, restriction between the wave loops allows the shape change of the waveforms in the sheath to be uniformly transmitted to the waveforms to be surrounded outside the sheath. Compared with a bare stent provided with wave loops having a suspended waveform/wave trough relationship, the bare stent may be more easily collected into the sheath, so that outward turns, as shown in FIG. 2-2, of the waveforms caused by squeezing and dragging during assembly, and even damage to the shape of the stent, can be avoided. Similarly, when the delivery system reaches the appointed position and slowly releases the stent from the sheath, the bare stent may maintain a good shape and be uniformly and gradually released from the sheath (FIG. 4-1), so that it is possible to avoid injury to the vessel wall caused by sudden change during expansion (FIG. 4-2) of the wave loops during release because of the restriction between the extremely free wave loops.

Three restrained connection points A of the bare stent of the present embodiment are uniformly distributed along the circumferential direction, and are spirally arrayed in the axial direction as shown in FIG. 3-2. All the other waveforms adopt the non-contact and mutually-suspended connection points B. Due to the axial tensile strength provided by the restrained connection points, the multilayer wave loop stent formed by adopting this arrangement has a stable structure, is low in axial elongation, and has a partially shortened space. The wave loops moving close to one another may provide the flexibility to a certain extent. The axially and spirally arrayed connection points A eliminate the directivity of the overall physical performance of the stent. The non-contact and mutually-suspended connection points B may enable the wave crests/wave troughs adopting this connection mode to be in relatively free and mutually non-interfering states. The wave loops have a certain displacement/deformation space in the axial direction and may move in a relative manner close to, or away from, each other to further improve the flexibility of the stent.

Embodiment 2

Figure 51:
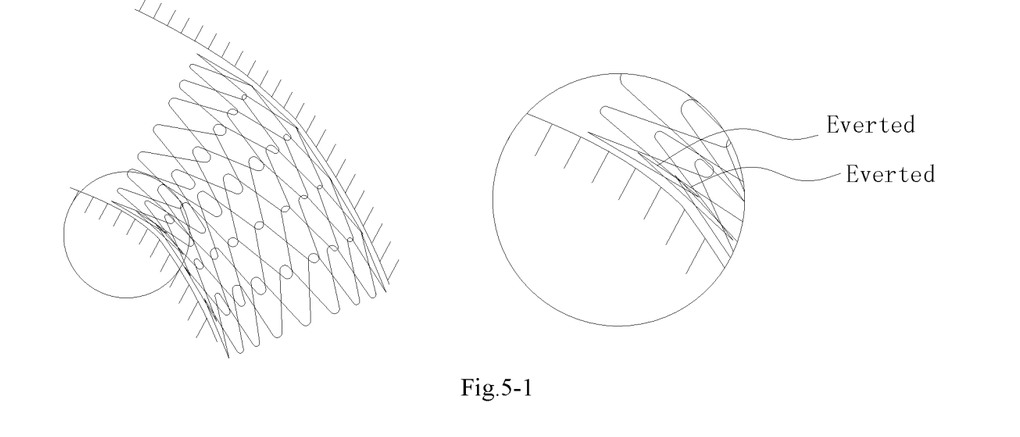
Figure 52:
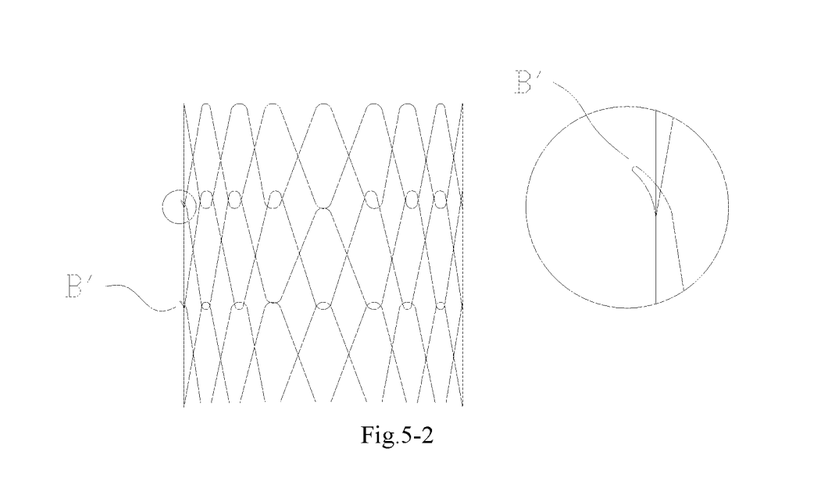
Figure 53:
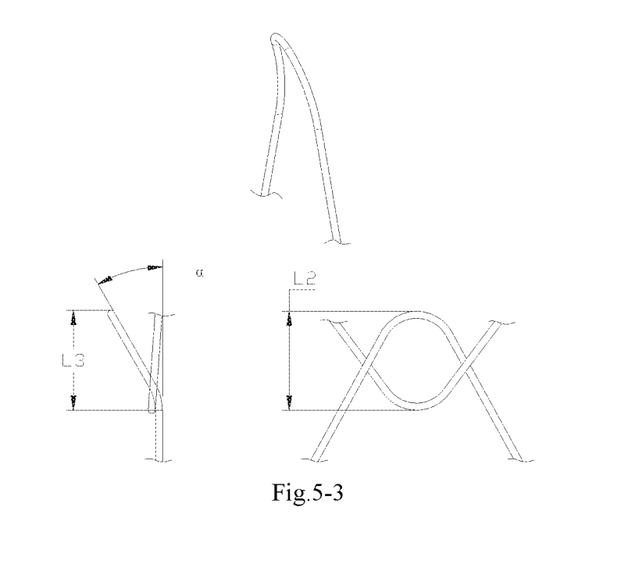
Figure 54:
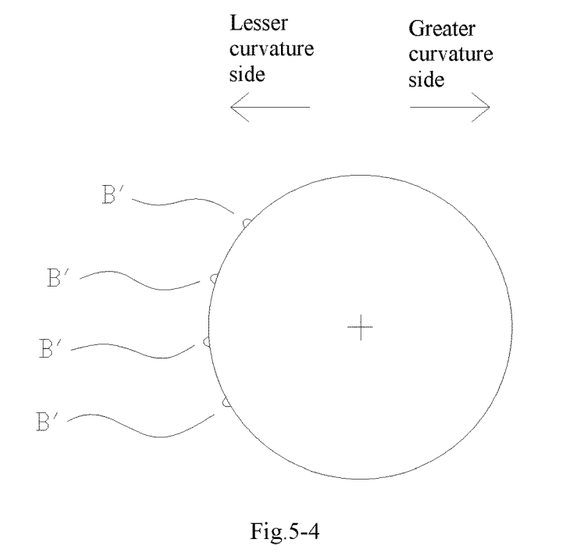
Figure 55:
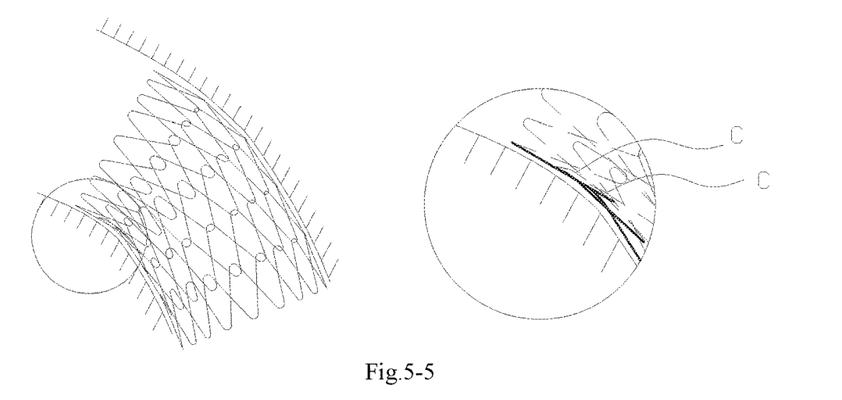

For the waveforms adopting the mutually suspended connection points B, the wave crests of the lower layer wave loop are relatively high. If the waveforms adopting the mutually suspended connection points B are located on the lesser curvature side of the stent, referring to FIG. 5-1, the stent would bend towards the lesser curvature side after being implanted into a bent vessel, the waveforms of two adjacent wave loops would mutually move/twist, and consequently the relatively high wave crests in the lower layer wave loop would be warped. In other words, the stent may not adhere to the vascular wall, which will result in a risk of scratching the vessel wall when the delivery system is withdrawn. In addition, the scratching of the delivery system and the wave loops may cause the waveforms to move. Moreover, the warping wave crests would have a certain impact on the hemodynamics.

Based on Embodiment 1, part of the connection points B located on the lesser curvature side of the stent are optimized so as to enable the wave crests in the connection points B to have an everted angle α (FIG. 5-2), and it is desirable that the angle α is between 20 and 30 degrees. The heights L3 of the everted angle along the axial direction of the bare stent are less than or equal to the distances L2 between the vertices of the wave crests of the lower layer wave loop and the vertices of the wave troughs of the upper layer wave loop, which are in the non-contact mutually-suspended connection for connection points B (FIG. 5-3). The everted connection points B are hereinafter referred to as connection points B'. In the present embodiment, each wave loop is composed of 15 wave crests/wave troughs. The connection mode for two adjacent wave loops is the same as that in Embodiment 1. Four connection points B, facing to the lesser curvature side, of the stent are everted and preset to form the connection points B' (FIG. 5-4). When the stent is released at the predetermined position, the connection points B' could effectively minimize the protrusion of the wave crests caused by the original connection points B (FIG. 5-5), so that the adherence of the lesser curvature side of the stent is better, and the risk of displacement/deformation/turning caused by scratching from the delivery system to the bare stent is lowered.

It is worth mentioning that if the connection points B' are arranged on the greater curvature side of the stent, the protruding everted angles α may not be adhered to the vessel wall, which would lead to the reduction of the adherence of the greater curvature side of the stent. The protruding preset part would stimulate the vessel wall and even injure the vessel wall, so that the number and positions of the connection points B' need to be designed with a proper clinical objective. When the stent needs to be adapted for use in a complicated and changing vascular environment, more connection points B' may be used on the lesser curvature side of the stent.

Embodiment 3

Figure 61:
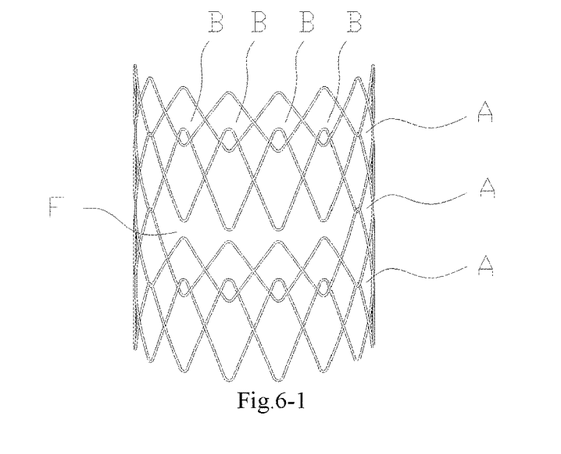
Figure 62:
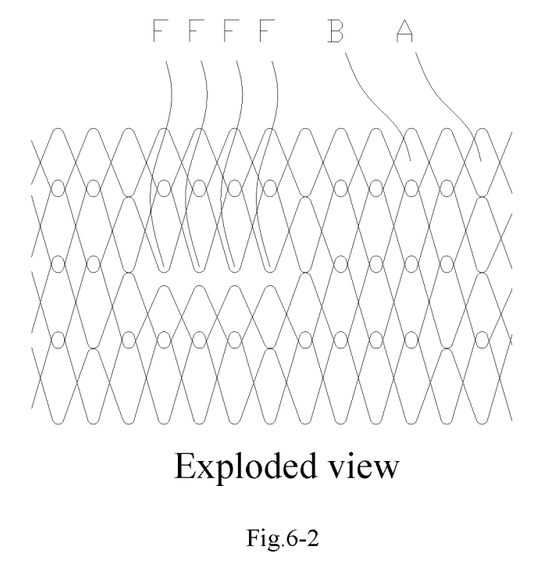
Figure 63:
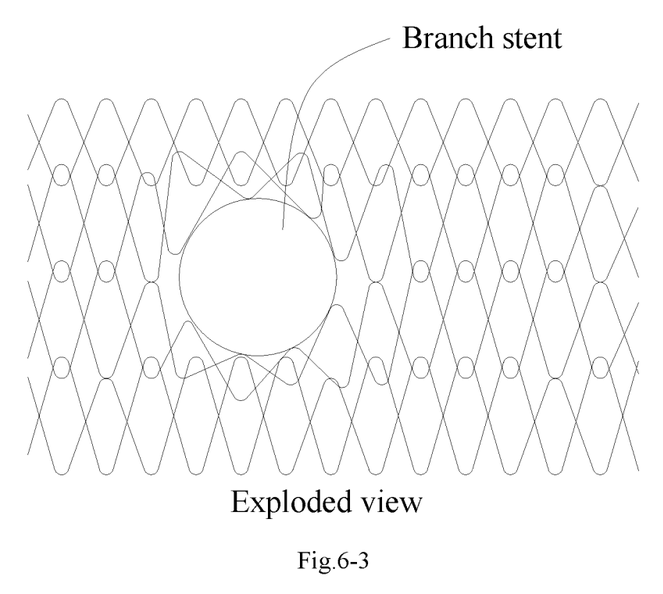

The bare stent of the present embodiment provides a simple solution for fenestration and placement of a branch stent during operation. Referring to FIG. 6-1, based on Embodiment 1, the waveforms on the side opposite to a branch vessel of the bare stent are adjusted. By controlling the shape and the elongation of the stent by retaining the connection points A, in a region to be fenestrated, 2 to 4 suspensions F (mutually suspended wave crests/wave troughs of the upper layer wave loop and the lower layer wave loop) are used to replace the corresponding connection points B (replacing 4 connection points is shown, for example, in FIG. 6-2). The replacement number is correspondingly adjusted according to the specific part where the stent is used, and the diameter size of the branch vessel. If the diameter of the branch vessel is larger, more connection points B should be replaced. When the stent is released, the connection points A would guarantee the basic shape and a relatively low elongation of the stent, and the connection points B and the suspensions F would provide relatively high flexibility for the stent. After the stent is located and released, the waveforms may be separated farther based on the original distance to provide a space for implantation (FIG. 6-3) of the branch stent on the waveform structure-adjusted part that has the suspensions F. A branch stent delivery may easily pass through the suspended regions formed by the suspensions F. Meanwhile, the suspensions F have relatively large degrees of freedom and the waveforms do not restrict one another, so the released branch stent would not suffer from relatively high rebound squeeze pressure from an aorta stent in the suspended region formed by the suspensions F, thereby guaranteeing the smooth blood flow of the branch vessel.

Embodiment 4

Figure 71:
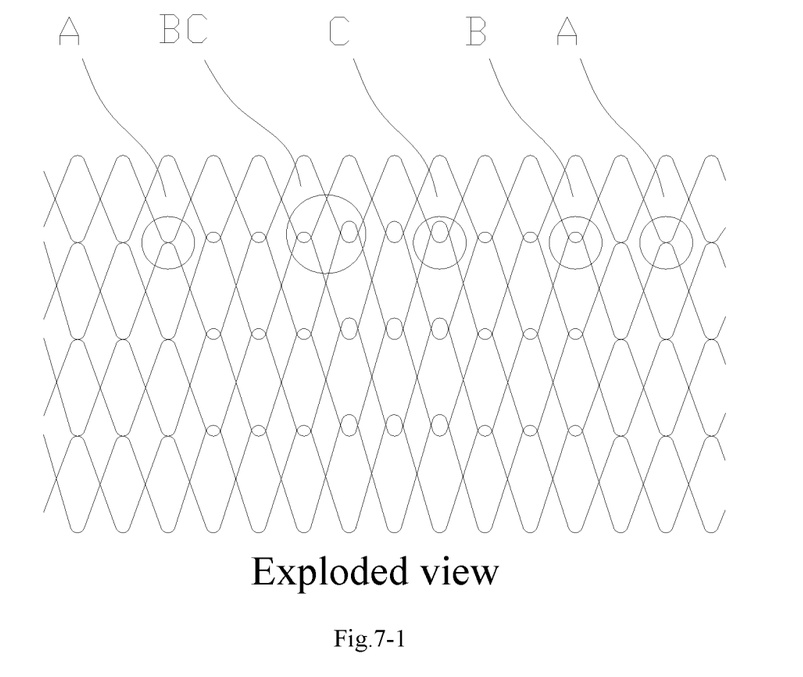
Figure 72:
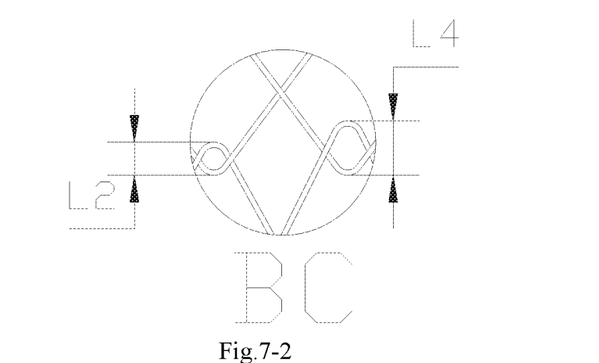
Figure 73:
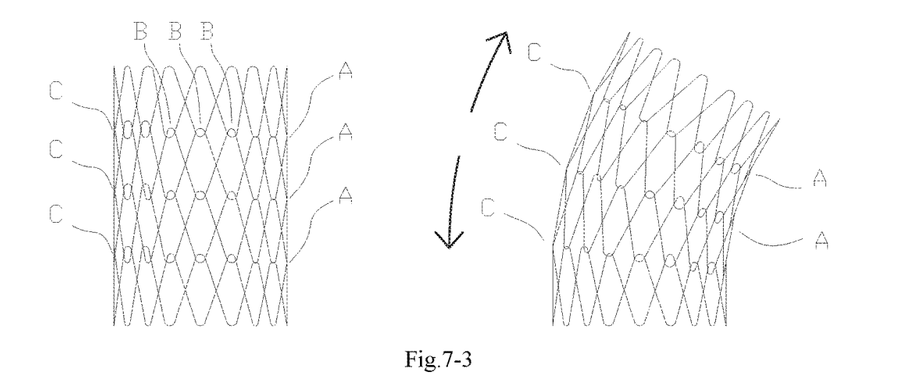

The bare stent (FIG. 7-1) of the present embodiment is an aorta restrictive woven bare stent for extending an anchoring region of a proximal end of an aorta stein. Each wave loop of the stent includes 15 wave crests/wave troughs. A connection mode between the upper layer wave loop and the lower layer wave loop can be as follows: 6 wave crests/wave troughs in every two adjacent wave loops on the lesser curvature side of the stent are in restrained connection by adopting the mutually restrained connection points A, and the other wave crests/wave troughs are all provided as non-contact and mutually-suspended connections. Three wave crests/wave troughs (connection points C) on the greater curvature side form a relatively large mutually-suspended overlapped region (L4 in FIG. 7-2), and each of both sides has 3 wave crests/wave troughs (connection points B) which form a relatively small mutually-suspended overlapped region (L2 in FIG. 7-2). A difference from Embodiment 1 lies in the fact that the overlapped regions of the wave crests and the wave troughs which correspond to the connection points of the non-contact and mutually-suspended connection of the present embodiment have different heights (B and C in FIG. 7-1), so that the stent can comply with the aorta included angle, and the adherence is further improved as well. When the stent complies with the aorta included angle, there are not too many warping wave crests/wave troughs that are produced on the inner wall of the stent. The lesser curvature side is smooth, and the greater curvature side opens fully and may be adhered to the wall completely (FIG. 7-3).

The overlapping heights of the connection points B and the connection points C may be achieved in various forms, including but not limited to: (1) adjusting the heights of the wave crests corresponding to the connection points; (2) adjusting the heights of the wave troughs corresponding to the connection points; and (3) adjusting the heights of both the wave crests and the wave troughs which correspond to the connection points.

Figure 74:
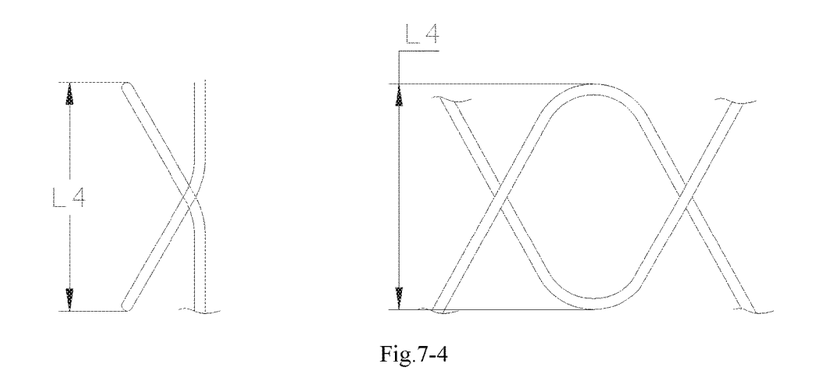

For a stent to be applicable to the bent vessel, the mode in Embodiment 2 may be adopted to enable the wave crests located on the lesser curvature side to have the vertex angle everted by an angle α, so as to lower the risk that the delivery system scratches the wave crests/wave troughs on the inner wall of the stent. When the stent adopts the form (2) or (3) to achieve a virtual-suspended connection between two adjacent wave loops, the wave crests and the wave troughs may both have the vertex angle everted by the angle α (FIG. 7-4), and the height L4 of each vertex angle everted along the axial direction of the bare stent is the same as that in Embodiment 2.

The arrangement mode and positions of combinations of connection points of unequal heights (combinations of the connection points B and the connection points C in the present embodiment) may be specifically adjusted according to specific clinical applications of the stent.

Embodiment 5

Figure 81:
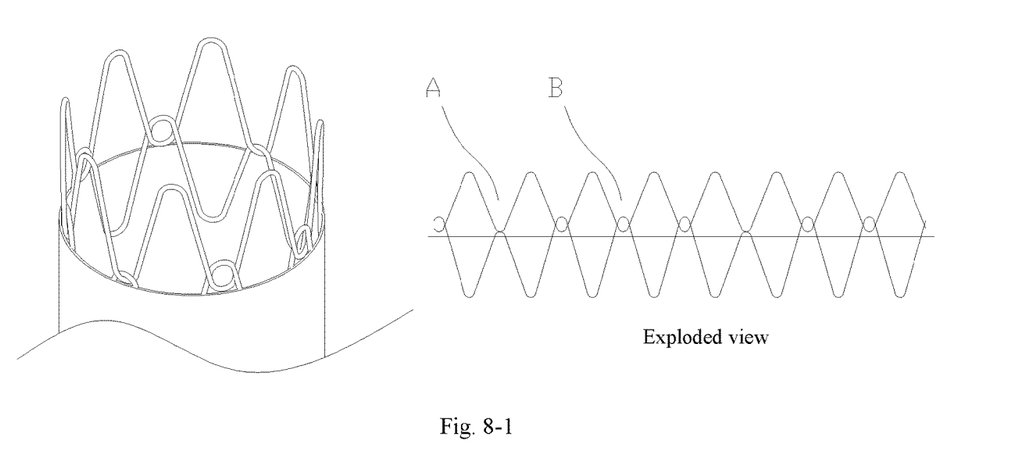
Figure 82:
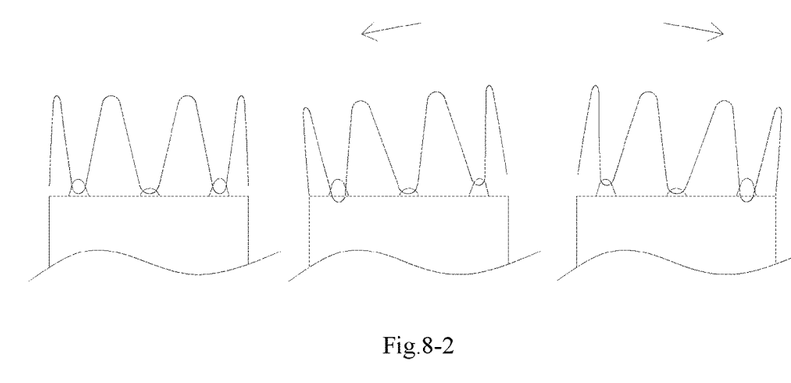
Figure 83:
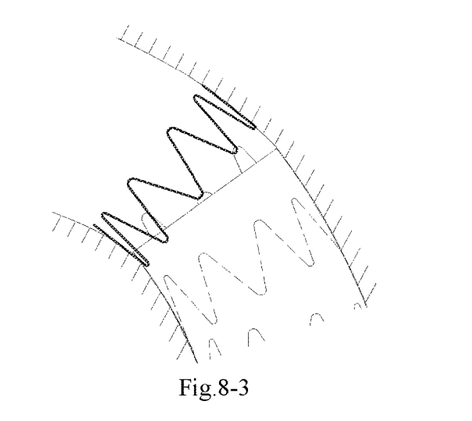

Referring to FIG. 8-1, the present embodiment provides a covered stent graft for an aorta. The proximal end of the stent graft is provided with two bare stent wave loops for extending an anchoring region. The lower layer wave loop is composed of multiple waveforms (including wave crests, wave troughs and rod bodies for connecting the adjacent wave crests and wave troughs) having different heights and arrayed along the circumferential direction, and is sutured on the inner side of the graft of the stent. The upper layer wave loop is composed of multiple waveforms (including wave crests, wave troughs and rod bodies for connecting the adjacent wave crests and wave troughs) having equal heights, and is connected with the lower layer wave loop through the wave crests/wave troughs (connection points A) in restrained connections, and the wave crests/wave troughs (connection points B) in non-contact mutually-suspended connections. A bare stent at the proximal end of the stent graft of the present embodiment has a certain swinging capacity (referring to FIG. 8-2), so that the stent graft may be better adhered and anchored in a blood vessel that has a certain angle, thereby effectively avoiding a beak phenomenon (see FIG. 8-3) that can be caused by the blood vessel having too large of an angle in the anchoring region.

Embodiment 6

Figure 91:
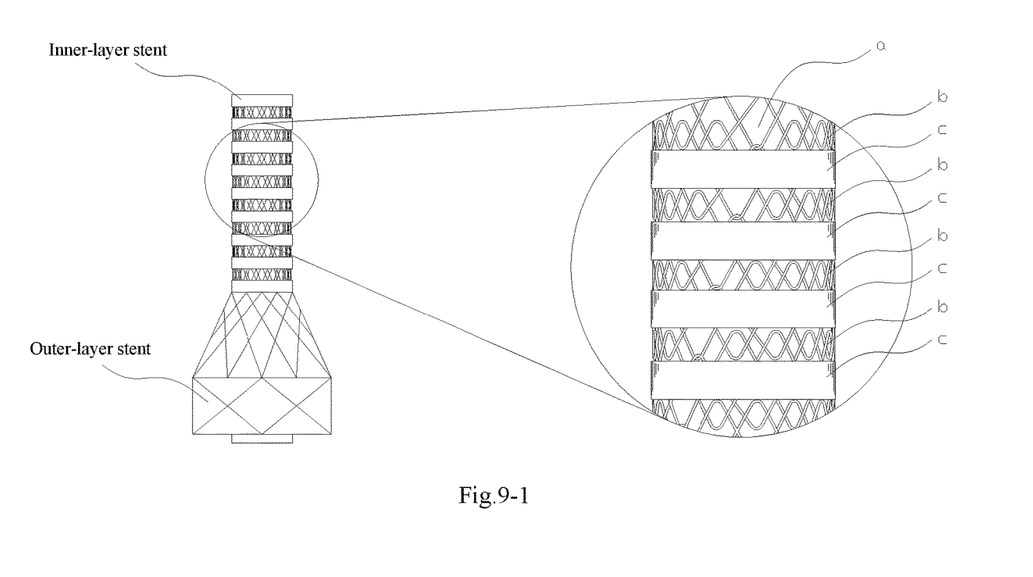
Figure 92:
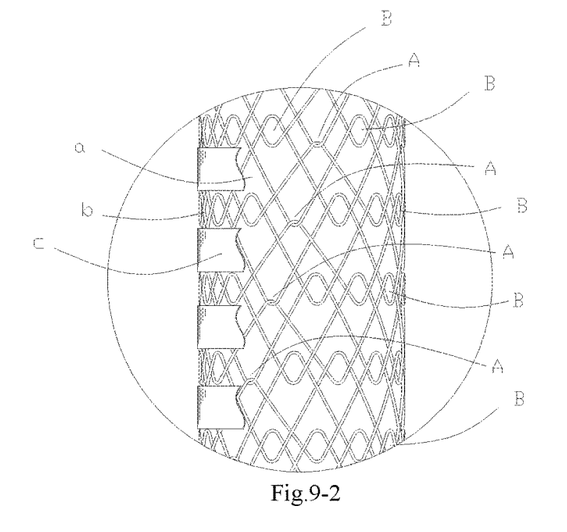

Referring to FIG. 9-1, the present embodiment provides a chimney stent that can be applied to a branch vessel and used cooperatively with an aorta stent graft. The chimney stent is a double-layer self-expansion type stent graft having an inner-layer structure and an outer-layer structure. The inner-layer stent is composed of an inner graft a, a metal stent b and an outer graft c. The inner graft a is an overall graft covering the inner wall of the metal stent b, and the outer membrane c is a segmented graft only covering the outer wall of the waveform of each wave loop of the metal stent b to expose connected portions between the wave loops. The metal stent b is formed by connecting multiple wave loops woven from nickel-titanium wires. To enable the stent to comply with the included angle between an aorta and the opening of a branch vessel, and to be flexible and effectively adhered, a connection mode of combining the wave crests/wave troughs (connection points A) in restrained connections, and the wave crests/wave troughs (connection points B) in non-contact and mutually-suspended connections, is adopted between the wave loops of the stent. There are two circumferentially distributed connection points A for mutually corresponding wave crests and wave troughs between every two wave loops, and the other wave crests and wave troughs are all connected by adopting the connection points B. The connection points A connect the entire stent in the axial direction in a spiral manner (FIG. 9-2). As the inner-layer stent has inner and outer-layer grafts, the number of the connection points on the metal stent is reduced to a minimum, and the capacity of the stent for complying with a vessel is maximized.

Embodiment 7

Figure 101:
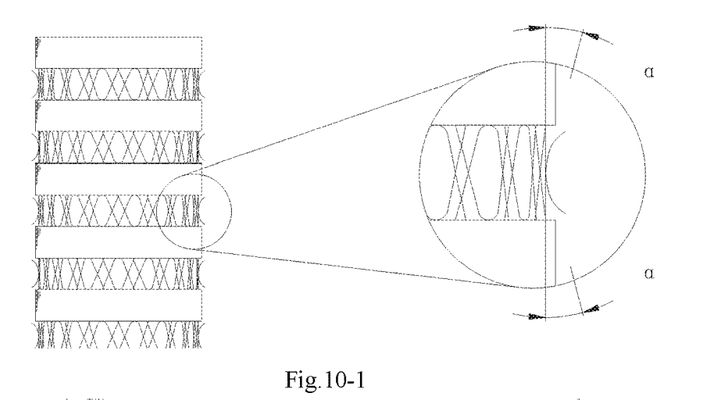
Figure 102:
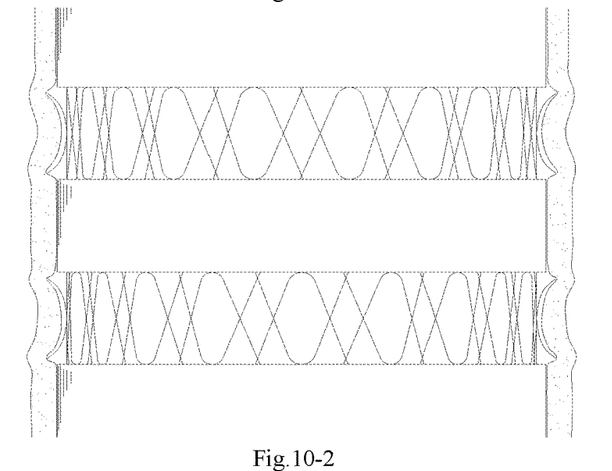

Based on Embodiment 6, the stent of the present embodiment is that all the connection points B have the vertex angle everted by the angle α. (FIG. 10-1). Through each protruding connection point, the anchoring force of the stent on the vessel wall is enhanced (FIG. 10-2), and the ability of the stent to resist movement is improved.

The embodiments of the present application are described above in combination with the accompanying drawings, but the present application is not limited to the above-mentioned specific implementation modes. The above-mentioned specific implementation modes are only schematic, not restrictive. Persons ordinarily skilled in the art can further make many forms under the enlightenment of the present application without departing from the aim of the present application and the scope protected by claims, and these forms shall all fall within the protection of the present application.

The invention claimed is:

1. A self-expanding vascular stent, comprising:
multiple wave loops arrayed along an axial direction and each wave loop having a first side and a second side, wherein in an expanded state, each group of two adjacent wave loops comprises a lower layer wave loop and an upper layer wave loop, and each lower layer wave loop and upper layer wave loop has a plurality of wave crests and a plurality of wave troughs, with each wave crest and each wave trough having a vertex;
wherein a first part of the wave crests of the lower layer wave loop and a first part of the wave troughs of the upper layer wave loop are in a restrained connection where the vertices of the wave troughs of the upper layer wave loop in an expanded state are in contact with the vertices of the wave crests of the lower layer wave loop, and
wherein vertices of a second part of the wave crests of the lower layer wave loop pass through vertices of a second part of the wave troughs of the upper layer wave loop to form non-contact and mutually-suspended connections, where the vertices of the wave troughs of the upper layer wave loop in the expanded state pass through the vertices of the wave crests of the lower layer wave loop by weaving from the either the first side or the second side of the upper layer wave loop to either the second side or the first side, respectively, of the lower layer wave loop, and the vertices of the wave troughs of the upper layer wave loop and the vertices of the wave crests of the lower layer wave loop extend in opposite directions and are separated by a distance.

2. The self-expanding vascular stent according to claim 1, wherein the wave crests which are in the non-contact and mutually-suspended connection with the wave troughs are located on a lesser curvature side region of the self-expanding vascular stent, and have a vertex angle everted by an angle α.

3. The self-expanding vascular stent according to claim 2, wherein the angle a is between 20 and 30 degrees.

4. The self-expanding vascular stent according to claim 2, wherein each vertex angle has a height, and the heights of the vertex angle everted along the axial direction of the self-expanding vascular stent are less than or equal to the distance when the wave crests of the lower layer wave loop and the wave troughs of the upper layer wave loop are in the non-contact and mutually-suspended connection.

5. The self-expanding vascular stent according to claim 1, wherein in a specific group of two adjacent wave loops, part of the wave crests of the lower layer wave loop and part of the wave troughs of the upper layer wave loop are in the restrained connection, and another part of the wave crests of the lower layer wave loop and corresponding wave troughs of the upper layer wave loop are suspended.

6. The self-expanding vascular stent according to claim 5, wherein 2 to 4 suspended wave crests and 2 to 4 suspended wave troughs are provided.

7. The self-expanding vascular stent according to claim 1, wherein the group of two adjacent wave loops further comprises wave crests and wave troughs which are both suspended.

8. The self-expanding vascular stent according to claim 7, wherein the vertices of all the wave troughs of the lower layer wave loop are located on a circular ring coaxial with an axis of the self-expanding vascular stent, and the lower layer wave loop which is tho in non-contact and mutually-suspended connection with the upper layer wave loop has different wave heights.

9. The self-expanding vascular stent according to claim 1, wherein distances between the vertices of at least two groups of wave crests and wave troughs which are in the non-contact and mutually-suspended connection are not equal.

10. The self-expanding vascular stent according to claim 1, wherein in the expanded state, the distance is ¼ to ⅓ of a waveform height of the wave troughs of the upper layer wave loop.

11. The self-expanding vascular stent according to claim 1, wherein the self-expanding vascular stent further comprises a stent graft section that has a first end, and the multiple wave loops form a bare stent which is connected with the first end of the stent graft section.

12. The self-expanding vascular stent according to claim 1, wherein the self-expanding vascular stent comprises an inner-layer stent and an outer-layer stent; the inner-layer stent having an outer surface, wherein the outer-layer stent is arranged outside and surrounds the inner-layer stent, and at least one end of the outer-layer stent is hermetically connected with the outer surface of the inner-layer stent; and wherein the inner-layer stent comprises a metal stent having a surface, and a graft covering the surface of the metal stent.

13. The self-expanding vascular stent according to claim 1, wherein part of the wave crests of the lower layer wave loop and part of the wave troughs of the upper layer wave loop are fixedly connected to form the restrained connection.

14. The self-expanding vascular stent according to claim 1, wherein part of the wave crests of the lower layer wave loop passes through part of the wave troughs of the upper layer wave loop and are in direct contact with the wave troughs to form the restrained connection.

* * * * *